United States Patent [19]

Wilson

[11] Patent Number: 4,544,780
[45] Date of Patent: Oct. 1, 1985

[54] CATALYTIC ISOMERIZATION OF TERTIARY OLEFINS

[75] Inventor: Stanley E. Wilson, Houston, Tex.

[73] Assignee: Shell Oil Company, Houston, Tex.

[21] Appl. No.: 604,358

[22] Filed: Apr. 27, 1984

[51] Int. Cl.$^4$ ............................................. C07C 5/24
[52] U.S. Cl. ................................... 585/377; 585/664; 585/668; 585/671; 585/947
[58] Field of Search ............... 585/377, 664, 668, 671, 585/947

[56] References Cited

U.S. PATENT DOCUMENTS 4,190,612  2/1980  Masilamani et al. ................. 585/378
4,227,028  10/1980  Masilamani et al. ................. 585/941

OTHER PUBLICATIONS

Masilamani et al., J. Org. Chem. (JOC Article), 48, 4918–4931, (1983).
Rogic, M. M. et al., J.A.C.S., 99, (15), pp. 5219–5220, (1977).

*Primary Examiner*—D. E. Gantz
*Assistant Examiner*—A. Pal

[57] ABSTRACT

A process for the isomerization of a tertiary double bonded olefin having a hydrogen atom attached to a carbon atom vicinal to the tertiary carbon of the double bond comprises treating the olefin in a solution of dry liquid sulfur dioxide in the presence of a catalyst selected from oxygen, a hydroperoxide or a protic acid or mixtures thereof.

6 Claims, No Drawings

CATALYTIC ISOMERIZATION OF TERTIARY OLEFINS

BACKGROUND OF THE INVENTION

1. Field of the Invention

The present invention relates to the catalytic isomerization of tertiary olefins.

2. Description of the Prior Art

U.S. Pat. No. 4,190,612 describes the isomerization of tertiary double bonded olefins in the presence of dry liquid sulfur dioxide. However, even in the presence of large amounts of sulfur dioxide the initial rate of reaction is slow.

It has now been found that the rate of the isomerization of tertiary double bonded olefins in the presence of dry liquid sulfur dioxide is substantially increased by the use of certain catalysts while at the same time the quantity of sulfur dioxide used in the isomerization is substantially decreased.

SUMMARY OF THE INVENTION

The present invention is directed to a process for the isomerization of an olefin having a hydrogen atom attached to a carbon atom vicinal to the tertiary carbon of the double bond, which process comprises treating the olefin in a solution of dry liquid sulfur dioxide in the presence of a catalyst selected from oxygen, a hydroperoxide or a protic acid or mixtures thereof.

The olefin starting material can be any tertiary double bonded material having a hydrogen atom attached to a carbon atom vicinal to the tertiary carbon of the double bond and which does not contain groups which would otherwise interfere with the reaction or with the catalyst selected therefore. The olefin to be isomerized can have the formula

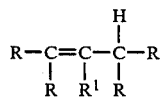

wherein each R independently is a hydrogen atom, or an alkyl, alkenyl, aryl, aralkyl, alkylaryl, cycloalkyl or substituted alkyl, substituted alkenyl or substituted aryl in which the substituents include halogen, mercapto, sulfonic acid and the like, or two adjacent R groups when taken together with the carbon atom to which they are attached form a cycloalkyl, cycloalkenyl or cyclopolyalkenyl group; ad $R^1$ is an alkyl, alkenyl, aryl, aralkyl, alkylaryl, cycloalkyl or substituted alkyl, substituted alkenyl or substituted aryl of the types described for R but selected independently thereof. Each of the groups R and $R^1$ or two adjacent R groups when taken together can be selected to give a total of up to about 30 carbon atoms in the olefin, preferably from about 5 to about 12 carbon atoms. For example, the tertiary carbon atom can be linked by a double bond to methylene, ethylidene, propylidene, butylidene, pentylidene, isopropylidene, isobutylidene, cyclohexylidene, cyclopentylidene, benzylidene, alkylidene, cycloalkylidene, arylalkylidene. The tertiary carbon atom can be linked by single bonds to a methyl, ethyl, propyl, isopropyl, butyl, isobutyl, pentyl, isopentyl, hexyl, heptyl, octyl, nonyl, decyl, cyclobutyl, cyclopentyl, cyclohexyl, cycloheptyl, cyclopentenyl, cyclohexenyl, 1-methylcyclohexenyl, benzyl, vinyl, alkyl, alkylene, arylalkyl group provided one of the ligands of one of the carbon atoms next to the tertiary carbon atom is hydrogen.

Non-limiting examples of olefinic starting materials for isomerization by the catalytic process of the invention include d-limonene (citrus limonene), dl-limonene (dipentene), terpinolene, pine oil by-products (dipentene and terpinolene mixtures), 1-(3-butenyl)-cyclohexene, 1-methyl-2-(3-butenyl)-cyclohexene, alpha-terpinene, gamma-terpinene, 1-alpha-phelladrene, d-alpha-phelladrene, (+), (−) or (±)-beta-pinene, methylene cyclohexane, 2-methyl pentene-1, 3-methyl pentene-2, 2,3-diphenyl propene, 2-methyl butene-1, 2-chloromethylbutene-1, 2-methyl butene-2, 2-methyl pentene-2, 2-ethyl butene-1, 2,3-dimethyl butene-1, 2,3-dimethyl butene-2, 2-methyl hexene-2, 3-methyl hexene-2, 2-ethyl pentene-1, 2,4,4-trialkyl-pentene-1 and -2, methylene cyclopropane, methylene cyclobutane, isopropylidine cyclopentane, 1-alkylcyclohexene, ethylidene cyclohexane, propylidene cyclohexane, 1-methyl-3-isopropylidene cyclohexane, 1-methyl-4-isopropylidene cyclohexane, 1-methyl cyclopropene, 1-methyl cyclohexene, 1-methyl-4-isopropylcyclohexene, 4-methyl-1-isopropylcyclohexene, 1-methyl cyclopentene, 1-phenyl-3-methyl butene-2, 1,2,3,3-tetraphenyl propene, 2,3-diphenyl butene-2, 2,4-diphenyl-4-methyl pentene-2, 1-methyl-2-(-1-naphthyl-ethyl)cyclopentene, 1-methyl-2-benzyl-4-isopropyl cyclohexene, 1-methyl-2-(1'-naphthyl)-cyclohexene, 1-methyl-2-(-3'-acenaphthylethyl)-cyclohexene, and 1-methyl-2-(-9'-phenanthryl ethyl)-cyclohexene.

In one embodiment of the invention, the olefinic starting material is a cyclohexene, an alkenyl-substituted cyclohexane in which the alkenyl group contains 1 to 3 carbon atoms or a bicyclo[1.1.3]heptane, each optionally substituted by one or more alkyl groups containing 1 to 3 carbon atoms or mixtures of such olefins, usually containing from 6 to about 10 carbon atoms, including as starting material pinene, methylene cyclohexane, 1-methylcyclohexene, 1-methyl-4-isopropylcyclohexene-3, pine oil by-products, alpha-terpinene, limonene and the like. The process is useful in the isomerization of limonene.

The olefinic product materials are known in the art and have a variety of uses as solvents, monomers and intermedites, e.g. to polymers and aroma and flavor chemicals and the like.

The catalyst is selected from oxygen, a hydroperoxide, or a protic acid or mixtures of these catalysts. Naturally, when oxygen is used, it can be substantially pure oxygen or a mixture of oxygen and an inert gas, such as nitrogen or argon or air. Any hydroperoxide which will not otherwise interfere with the reaction can be used. For convenience, the hydroperoxide is usually an alkyl or aralkyl hydroperoxide of up to about 12 carbon atoms, for example, tert-butyl hydroperoxide, cumene hydroperoxide, tert-pentyl hydroperoxide, benzoyl hydroperoxide, and the like. Tert-butyl hydroperoxide is the preferred hydroperoxide. Any protic acid which will not otherwise interfere with the reaction can be used. The protic acid is preferably a relatively strong acid, including sulfuric or sulfonic acids or ion exchange resin acids. For convenience, the protic acid is usually an alkyl- or arylsulfonic acid of up to about 12 carbon atoms, for example, methanesulfonic, ethanesulfonic, p-toluenesulfonic, m-nitrobenzenesulfonic, 2,4-diethylbenzenesulfonic or benzenesulfonic acid and the like. Of these, methanesulfonic acid is preferred. Preferably, the catalyst is oxygen or a hydroperoxide optionally with a strong protic acid. Good results are obtained with tert-butyl hydroperoxide.

Both water and alcohols appear to be detrimental in the isomerization reaction. Thus, it is desirable to conduct the reaction under substantially anhydrous conditions by using dry sulfur dioxide. When hydroperoxides, acids and the like are employed as catalyst, it is desirable to avoid using substantially aqueous solutions of such materials.

An advantage of the present process is that the rate of isomerization of olefins having a tertiary carbon at the double bond is substantially increased by use of the catalyst, while at the same time the amount of dry liquid sulfur dioxide used is substantially reduced.

The isomerization can be conducted at normal pressures and temperatures. At normal reaction pressures of about 0 and up to about 70 pounds per square inch, the reaction is conveniently conducted at a temperature in the range of from about 0° C. to about 70° C. and, preferably, at ambient temperatures, from about 15° C. to about 40° C.

The ratios of the ingredients in the process can vary. The weight ratio of sulfur dioxide to olefinic starting material is usually from about 1:1 to about 5:1 and preferably from about 1:1 to about 2.5:1, and especially from about 1:1 to about 1.5:1.

The amount of catalyst used can vary. The weight ratio of catalyst to olefinic starting material is usually in the range of from about 0.01% to about 10%, preferably from about 0.1% to about 1%.

No solvents are usually added to the reaction mixture; however, the presence of compatible solvents, e.g. hydrocarbons, halogenated hydrocarbons and the like is within the scope of the invention. It is also contemplated that the process of the invention be conducted by conventional techniques of batch, continuous or semi-continuous processes as may be individually preferred.

The reaction is conducted by dry sulfur dioxide being condensed in a (pressure) vessel previously charged with the olefin to be isomerized and the desired catalyst. (When the catalyst is other than oxygen or mixture of catalyst containing oxygen, one may choose to sparge the vessel with dry nitrogen to remove oxygen.) The reaction mixture and closed vessel are warmed to about room temperature, preferably while stirring magnetically. A pressure increase to about 20 to 50 pounds per square inch usually results. The isomerized product olefinic material is separated and recovered from the process by conventional techniques known in the art. For example, by stripping off the sulfur dioxide, neutralizing any acids formed for removal as salts and distillating or extracting, e.g. with methylene chloride, to remove by-products.

ILLUSTRATIVE EMBODIMENTS

The following embodiments are provided for the purpose of illustrating the invention and should not be regarded as limiting the scope of the invention in any way.

EMBODIMENTS I-V

The process was conducted at 25° C. in a thoroughly dried and base-washed pressure bottle equipped with a pressure gauge and sulfur dioxide inlet. A nitrogen atmosphere was maintained throughout the apparatus during the process. After the addition of 10 g of limonene and desired amount of catalyst, e.g. tert-butyl hydroperoxide (TBHP), the pressure bottle was immersed in a Dry Ice-isopropanol bath and about 10 to about 40 g of anhydrous sulfur dioxide was condensed in the bottle. The reaction mixture was allowed to warm to room temperature for a period of time dependent upon the desired level of conversion. The reaction was terminated by venting the sulfur dioxide and removing of residual amounts of sulfur dioxide by reducing the pressure to 50 mm. The reaction mixture was transferred to a distillation flask containing 100 ml of 0.1N aqueous sodium hydroxide and steam distilled. The phases of the distillate were separated and the organic layer was recovered as the desired product. The results of several such experiments run with varying ratios of anhydrous sulfur dioxide to limonene are set out in Table I below.

TABLE I

| \multicolumn{5}{c}{SULFUR DIOXIDE-CATALYZED ISOMERIZATION OF LIMONENE} |
|---|---|---|---|---|
| Embodiment | $SO_2$/Limonene (wt) | TBHP (g) | Limonene Conversion (%) | Terpinolene Selectivity |
| I | 0.62 | 0.03 | 22 | 80 |
| II | 1.22 | 0.03 | 40 | 85 |
| III | 1.90 | 0.03 | 70 | 73 |
| IV | 2.59 | 0.03 | 82 | 68 |
| V | 3.35 | 0.03 | 86 | 63 |

Following procedures similar to those described for Embodiments I-V, above, limonene was isomerized with anhydrous sulfur dioxide in the presence of catalysts selected from oxygen, methanesulfonic acid, benzoyl peroxide, trifluoroacetic acid and an acidic ion exchange resin.

What is claimed is:

1. A process for the isomerization of an olefin having a hydrogen atom attached to a carbon atom vicinal to the tertiary carbon of the double bond, which comprises treating the olefin in a solution of dry liquid sulfur dioxide in the presence of a hydroperoxide catalyst.

2. A process according to claim 1 wherein the catalyst is an alkyl or aralkyl hydroperoxide of up to about 12 carbon atoms.

3. A process according to claim 2 wherein the catalyst is tert-butyl hydroperoxide.

4. A process according to claim 1 wherein the olefin is a cyclohexene, an alkenyl-substituted cyclohexene in which the alkenyl group contains from 1 to 3 carbon atoms or a bicyclo[1.1.3]heptene, each optionally substituted by one or more alkyl groups containing 1 to 3 carbon atoms or mixtures of such olefins.

5. A process according to claim 1 wherein the olefin is limonene.

6. A process according to claim 3 wherein the olefin is limonene.

* * * * *